United States Patent [19]

Takaku et al.

[11] 4,275,056

[45] Jun. 23, 1981

[54] HGI-GLYCOPROTEIN CAPABLE OF STIMULATING PROLIFERATION AND DIFFERENTIATION OF HUMAN GRANULOCYTE, PROCESS FOR PREPARING SAME AND LEUKOPENIA CURATIVE CONTAINING SAME

[75] Inventors: Fumimaro Takaku, Utsunomiya; Katsuhiro Ogasa, Yokohama; Morio Kuboyama, Tokyo; Minoru Saito, Komae; Nobuya Yanai, Tokyo; Masayuki Nishida, Osaka, all of Japan

[73] Assignees: Morinaga Milk Industry Co., Ltd., Tokyo; The Green Cross Corporation, Osaka, both of Japan

[21] Appl. No.: 22,594

[22] Filed: Mar. 19, 1979

[30] Foreign Application Priority Data

Mar. 20, 1978 [JP] Japan ................... 53-31999

[51] Int. Cl.³ ...................... A61K 35/22; C07G 7/00
[52] U.S. Cl. ................................. 424/99; 260/112 R; 424/101; 424/177
[58] Field of Search .............. 260/112 R; 424/99, 177

[56] References Cited

U.S. PATENT DOCUMENTS 4,178,285   12/1979   Felts et al. ................. 424/99 X

OTHER PUBLICATIONS

Australian J. of Exp. Biology and Medical Science, vol. 47, pp. 467–483 (1969), Stanley et al.
Blood, vol. 49, No. 4, 1977, pp. 573–583, Burgess et al.
J. of Cellular Physiology, vol. 78, 1975, pp. 451–459, Sheridan et al.
Diabetologia, 5, 192–194 (1969), Devlin et al.
Zeitschrift fuer Klinische Chemie und Klinische Biochemie, vol. 8, No. 3 (1970), pp. 288–292, Von D. Grasslin et al.
Kellar et al., Proc. of the Soc. for Exp. Biology and Medicine, 150, pp. 766–772 (1975).
Bourrillon, Proteins in Normal and Pathological Urine, pp. 20–44, Karger, Basel/New York (1970).
Chem. Abstracts, vol. 55, 1961, 716g–717a, Bourillon et al.
Kellar et al., *Fed. Proceed.*, vol. 33, No. 4, 681 (1974).
Kellar et al., *Chem. Absts.*, vol. 84: 71,099j (1976).
Wieslander et al., *Clin. Chim. Acta,* 78(3), pp. 391–400 (1977).
Carrea et al., *Bichim. Biophys. Acta,* 295(1), pp. 274–282 (1973).

*Primary Examiner*—Howard E. Schain
*Attorney, Agent, or Firm*—Cushman, Darby & Cushman

[57] ABSTRACT

A colony-stimulating factor having definite physical and chemical properties and a function of stimulating activity on human bone marrow cells to proliferate and differentiate, thereby forming granulocyte colonies, is obtained from human urine by concentrating the urine with respect to proteins contained therein by adsorption chromatography with silica gel, salting out with ammonium sulfate and other means, then removing impurities by adsorption on cation exchanger, and further purifying by ion exchanging chromatography on anion exchanger, gel filtrating chromatography with highly crosslinked gels, affinitive chromatography with sugar affinitire adsorbents and electrophoresis.

24 Claims, 4 Drawing Figures

HGI-GLYCOPROTEIN CAPABLE OF STIMULATING PROLIFERATION AND DIFFERENTIATION OF HUMAN GRANULOCYTE, PROCESS FOR PREPARING SAME AND LEUKOPENIA CURATIVE CONTAINING SAME

This invention relates to a glycoprotein (hereinafter referred to as HGI-glycoprotein, wherein HGI means "human granulocyte inducing".) isolated from urine of normal humans, which acts on granulopoietic stem cells in human bone marrow, thereby stimulating the proliferation and differentiation of said cells to form granulocytes; a method for the preparation of said glycoprotein; and curatives for leukopenia containing said glycoprotein.

Although the peripheral blood of a healthy human contains 5,000 to 9,000 leukocytes per 1 mm$^3$, that of a patient of leukopenia contains below 5,000 leukocytes per 1 mm$^3$. Such a symptom of reduction in the count of leucocytes is called leukopenia. Leukopenia is associated with anomalous decrease of proliferation of bone marrow cells by some diseases, various lesions in bone marrow, exposure to radiation or administration of carcinostatic substances. For the therapy to leukopenia, there have been employed chemotherapeutics containing glycyrrihizin or cysteine-glycine as active ingredient, α-mercaptopropionylglycine, or Cepharantin, a kind of alkaloid. These chemotherapeutics, however, are undesirable because of insufficient effectiveness and side effects. Accordingly, many researchers have been in progress in recent years to develop therapeutical substances for treating leukopenia which are more effective with less side effects. It was known that colony-stimulating factor (hereinafter referred to as CSF) stimulates the proliferation and differentiation of bone marrow cells. CSF acts on bone marrow cells and stimulates the proliferation and differentiation to form granulocyte or macrophage. It is an essential factor for the marrow cells, when cultured in vitro, to form granulocytic or macrophage cell aggregates (hereinafter referred to as granulocytic or macrophage colony) by simultaneous proliferation and differentiation [Ichikawa, Y., Proceedings of the National Academy of Science, Vol. 56, p. 488 (1966); Metcalf, D., Experimental Hematology, Vol. 1, p. 185 (1973)]. Since CSF induced the granulocytic and macrophage colonies from bone marrow cells, some of the researchers suggested that CSF should be regarded as separate factors that is, granulocyte inducing factor and macrophage inducing factor [Stanley, E. R. et al, Journal of Experimental Medicine, Vol. 143, p. 631 (1976)]. However, in general, these factors are assayed collectively as CSF in vitro assay by mouse bone marrow cells. Many factors stimulating colony, formations in vitro by mouse bone marrow cells having been isolated from various sources i.e. serum, urine, various organ extracts, and media conditioned by various tissues and cell lines, body fluid elements such as serum and urine; conditioned media of cells such as leucocyte, and tissues [Sheridan, J. W., Journal of Cell Physiology, Vol. 78, p. 451 (1971)]. CSF which acts on human bone marrow cells have been isolated from human origin i.e. various organ extracts, serum, media conditioned by tissues [Metcalf, D. and Moore, M. A. S., "Ciba Foundation Symposium 13, Haemopoietic Stem Cells", p. 157, Elsevier Excerpta Medica, Holland (1973)]. However, each CSF obtained from various organs, various cells and conditioned media thereof is not a single substance common to every sources. For instance, the molecular weight of CSF obtained from the media-conditioned by human placental cells is 30,000 dalton [Burgess, A. W. et al, Blood, Vol. 49, p. 573 (1977)], while that of CSF from human serum is 45,000 dalton [Chan, S. H. et al, British Journal of Haematology, Vol. 20, p. 329 (1971)]. Two types of CSF having molecular weights of 35,000 and less than 1,300 were isolated from media conditioned by human leukocyte [Price, G. B. et al, Blood, Vol. 42, p. 341 (1973)]. Furthermore, each CSF has different activity, some acting on either type of cells to be proliferated and differentiated to granulocyte or macropharge, others on both types of cells. Therefore, CSF's isolated from different sources are considered to be substances different from one another [Metcalf and Moore, loc. cit., (1973)].

It is also known that in human urine, there exists a type of CSF which is capable of stimulating mouse bone marrow cells to form colonies of granulocytes and macrophages in vitro [Stanley, E. R. et al., Federation Proceedings, Vol. 34, p. 2272 (1975); Stanly, E. R. and Metcalf, D., Australian Journal of Experimental Biology and Medical Science, Vol. 47, p. 467 (1969)]. It was reported that this CSF has a molecular weight of 45,000 and stimulates the proliferation and differentiation by mouse bone marrow cells to form a macrophage dominant colony. In contrast to its stimulating effect on mouse bone marrow cells, it rarely stimulates the formation of granulocytic or macrophage colony by human bone marrow cells but consistently stimulates the formation of clusters. In this specification, with respect to human bone marrow cells, the terms "colony" and "cluster" mean cell aggregates containing 40 or more cells and 3 to less than 40 cells, respectively, in accordance with the definition of Metcalf [Metcalf, D., Experimental Hematology, Vol. 2, p. 157 (1974)].

The present inventors engaged in studies on the substances having CSF activity in human urine and, as a result, found and isolated in purified state a novel HGI-glycoprotein which, quite different from the above-said known CSF, has a molecular weight of about 85,000 and acts both human and mouse bone marrow cells to form pure granulocytes colonies in vitro. Further, the present inventors succeeded in purification of the HGI-glycoprotein isolated from human urine which remarkably acts on human bone marrow cells and stimulates the proliferation and differentiation of pure granulocytes colonies (hereinafter sometimes referred to as biological activity). Further, this HGI-glycoprotein was identified, preparative method thereof with good reproducibility was developed, and uses were found, leading to the accomplishment of this invention.

An object of this invention is to provide a novel CSF.

Another object of this invention is to provide a method for the preparation of this novel CSF.

A further object of this invention is to provide a therapeutic agent for leukopenia, which contains the novel CSF.

According to this invention there is provided a glycoprotein from the human urine, which stimulates human bone marrow cells to form colonies of granulocytes and which has a molecular weight of 75,000 to 90,000 dalton as determined by gel filtration.

The HGI-glycoprotein of the invention is produced by concentrating human urine with respect to proteins contained therein, contacting the urinary proteins with a cation exchanger to remove impurities by adsorption on said exchanger, contacting the effluent with an anion exchanger to adsorb the active material, eluting the active material with a saline solution according to linear concentration gradient elution, subjecting the eluate to gel filtration chromatography on a highly crosslinked polymer gel to develop the active material, collecting fractions of a relative effluent of 1.11 to 1.60, subjecting the collected fractions to affinity chromatography with a sugar affinitive absorbent to adsorb the active material, eluting the adsorbed active material with a 20-100 mM saccharide solution, subjecting the eluate to preparative zone electrophoresis, eluating the active material with saline solution and recovering the active material in pure form.

The invention is described below in details.

A typical procedures to prepare the HGI-glycoprotein of this invention is carried out in the following way. Fresh urine collected from normal humans is adjusted to pH 6-9, preferably 7-8, with dilute acid solutions or alkaline solutions and then centrifuged to remove insolubles contained in the urine. The supernatant is contacted with a silicon-containing adsorbent such as silica gel, silica gel-magnesium silicate, diatomaceous earth, silica glass or bentonite and the adsorbed constituents were eluted with an alkaline solution of preferably pH 9 or higher. The alkaline solution which used for the elution is not specific, but is preferably an aqueous solution of ammonium hydroxide, sodium hydroxide or the like in a concentration of 0.3 to 1.5 M. The eluate thus obtained is adjusted to pH 7-8 with acid solution and added with a neutral salt such as, for example, ammonium sulfate to 70% saturation to salt out the active substance, whereby a crude protein fraction containing the HGI-glycoprotein is obtained.

The above crude protein fraction is re-dissolved in a small portion of an alkaline solution, freed from low molecular substances by ultrafiltration diluted with a saline buffer solution and contacted with a cation exchanger (for example, carboxymethyl dextran, carboxymethylcellulose or phosphocellulose) to remove the impurities contained in this solution. The above contact is carried out in the condition of neutral pH, and the crude fraction of HGI-glycoprotein and the cation exchanger have been adjusted to pH 6-8 with preferably 0.01-0.15 M saline buffer solutions before the contact. Most of the HGI-glycoprotein passes through the cation exchanger without adsorption after concentration, the concentrated effluent is equilibrated with a dilute buffer solution of pH 6-8 and applied to ion-exchange chromatography with an anion exchanger, e.g. DEAE-cellulose, which has been equilibrated with the same buffer, the HGI-glycoprotein is adsorbed onto the anion exchanger. Then, the adsorbed HGI-glycoprotein is eluted by the method of so-called linear concentration gradient elution by using a 0.1-0.3 M saline solutions such as sodium chloride. The HGI-glycoprotein is eluted as a salt concentration of 0.1 M or higher but a perfect separation is difficult. The fractions of effluent at 0.1-0.3 M salt concentration are collected and, if necessary, is subjected to desalting and concentration treatments.

It is also possible that the step-wise elution with 0.1-0.3 M saline solution are applied to elute the HGI glycoprotein from the ion exchanger.

For the purpose of further purification, the combined fraction obtained above is applied to gel filtration chromatography on a highly crosslinked polymer gel having a water regain value of 10-20 ml/g such as, for example, Sephadex ® G-150 or Biogel ® P-100 and the active substances are developed with a 0.05-0.1 M saline buffer solution. Fractions of a relative effluent volume of 1.11 to 1.60, preferably 1.11 to 1.45, are collected, desalted and concentrated or lyophilized.

The thus obtained semi purified substances containing HGI-glycoprotein can be used as pharmaceuticals.

The relative effluent volume as herein referred to is a volume expressed by the ratio Ve/Vo (where Ve represents the volume of solvent necessary to elute the substance existing in the column and Vo represents the void volume of the column).

For further purification, the semi purified substances, obtained above is dissolved in dilute saline buffer solution containing 1.0-2.0 M such as, for example, a phosphate buffer solution at pH 6.0-8.0, preferably 6.0-7.0, containing 1.0-2.0 M NaCl and applied to affinity chromatography with a sugar affinitive absorbents such as, for example, concanavalin A-Sepharose 4B (supplied by Fine Chemical Laboratory), which has been equilibrated with the same buffer solution. The HGI-glycoprotein adsorbed on affinity column is eluted with a 1.0-2.0 M saline in dilute buffer containing a 20-100 mM saccharides in dilute buffer solution containing 1.0-2.0 M salt at pH 6.0-8.0, for example, saccharide is α-methyl-D-glucoside or the like at pH 6.0-8.0, preferably 6.0-7.0. The fractions containing the HGI-glycoprotein are collected and, if necessary, desalted and concentrated or lyophilized.

For still further purification of the HGI-glycoprotein by electrophoresis, the combined fraction obtained from affinity chromatography are applied to preparative zone electrophoresis using as supporting medium an acrylamide gel or agarose gel, pH 7.0-9.0, and the highly purified the HGI-glycoprotein is recovered from the supporting medium with a dilute saline solution under cooling conditions, desalted and concentrated or lyophilized.

According to this invention, it is possible to recover urokinase, callicrein and lysozyme from human urine during the course of preparing HGI-glycoprotein.

The HGI-glycoprotein thus obtained is a powder which is white or faint brown in color, is tasteless, odorless and slightly hygroscopic and has the physical and chemical properties as described below.

The physical and chemical properties were determined on sample No. 6 of Example 1 (described later).

(1) Molecular weight

The molecular weight of the HGI-glycoprotein of this invention was found to be about 85,000 dalton as measured by sodium dodecyl sulfate-polyacrylamide gel electrophoresis and 75,000 to 90,000 dalton as measured by gel filtration using Sephadex ® G-150. Accordingly, the most reliable molecular weight range seems to be from 75,000 to 90,000 dalton.

(2) Solubility

The solubilities of the HGI-glycoprotein in various solvents are as shown in Table 1.

TABLE 1

| Solvent | Solubility |
| --- | --- |
| Water | Soluble |
| Ethyl alcohol | Insoluble |
| Acetone | Insoluble |
| Chloroform | Slightly soluble |
| 1 M Sodium chloride solution | Soluble |
| 10% Sucrose solution | Soluble |

Beside, it is easily soluble in a dilute saline solution such as, for example, a dilute phosphate solution or a dilute trisaminomethane solution. It is also soluble in a dilute saline solution in the pH range from 1 to 12.

(3) pH

The pH of a 1% aqueous solution of HGI-glycoprotein is 5.0 to 6.0, that is, in the acidic range.

(4) Specific optical rotation.

The optical rotation was measured on a 0.25% aqueous solution of HGI-glycoprotein at 20° C. The specific optical rotation $[\alpha]_D^{20}$ was found to be in the range of $0 \pm 40$.

(5) Infrared absorption spectrum.

Figure 1:
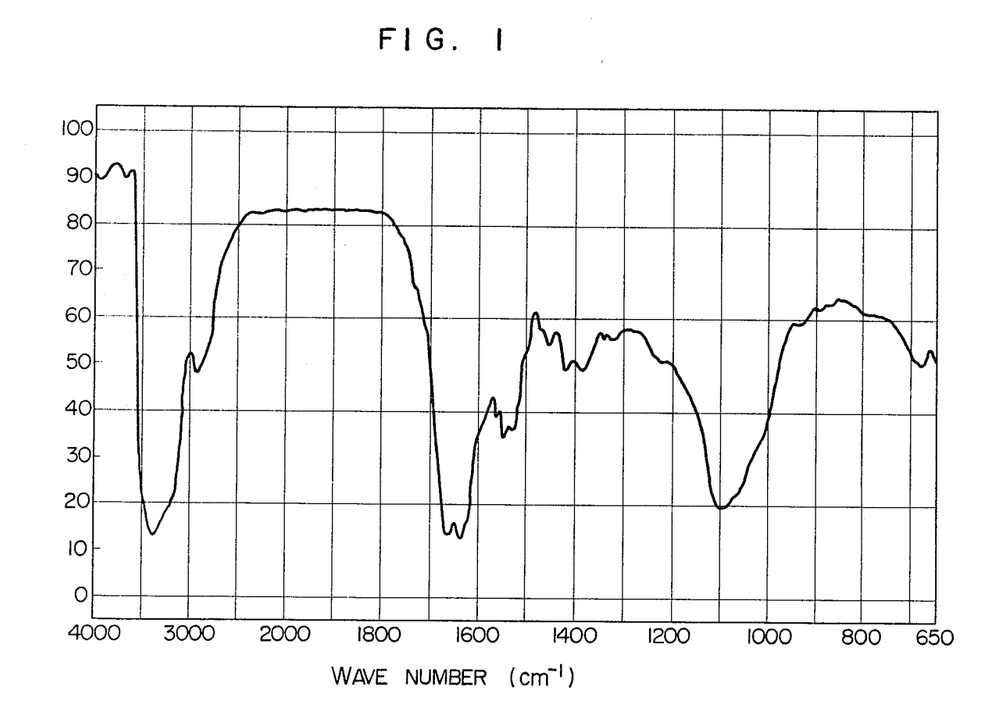
FIG. 1 represents infrared absorption spectrum of the HGI-glycoprotein.

The infrared absorption spectrum of HGI-glycoprotein as measured by the method of KBr pellets is as shown in FIG. 1. The characteristic absorption bands are as shown in Table 2.

TABLE 2

| Absorption wave number (cm$^{-1}$) | Degree of absorption | Remarks |
| --- | --- | --- |
| 3600–3200 | Strong | The broad absorption band seems to be originated from the ν—OH groups forming various degrees of hydrogen bands. |
| 1700–1600 | Strong | The broad absorption band seems to be originated from —CO . NH—bonds of protein fragment. |
| 1550 | Medium | |
| 1430–1380 | Medium | |
| 1150–1000 | Medium | The broad absorption band seems to be originated from —C—O—C—bonds of polysaccharide fragment. |

(6) Isoelectric point

The isoelectric point of HGI-glycoprotein is pH $4.7 \pm 0.2$, as measured by polyacrylamide gel isoelectric focussing.

(7) Color reaction

Various color reactions were examined on HGI-glycoprotein dissolved in water. The results obtained are as shown in Table 3.

TABLE 3

| Color reactions | Developed color | Remarks |
| --- | --- | --- |
| Lowry-Folin's reaction | Blue | Peptide bonds |
| Ninhydrin reaction (hydrolyzed with 6N HCl at 110° C. for 2 hours) | Violet | α-amino acids |
| α-Naphthol-sulfuric acid reaction (Molisch's reaction) | Violet | Saccharides |
| Indole-sulfuric acid reaction (Dische's reaction) | Brown | " |
| Anthrone-sulfurica acid reaction | Dark green | " |
| Phenol-sulfuric acid reaction | Brown | " |

(8) Thermostability

On heating a 1% aqueous solution of HGI-glycoprotein at $60° \pm 0.5°$ C. for 30 minutes, the CSF activity was no more detectable.

(9) Amino acid composition of the protein fragment

HGI-glycoprotein was hydrolyzed with 1 N hydrochloric acid at 110° C. and the amino acid composition of the protein fragment was determined by means of an amino acid autoanalyzer to obtain the results as shown in Table 4.

TABLE 4

| Amino acid | Weight % | Mole (mM) |
| --- | --- | --- |
| Proline | 3.2 | 0.392 |
| Aspartic acid | 9.8 | 1.038 |
| Threonine | 2.8 | 0.331 |
| Serine | 11.9 | 1.596 |
| Glutamic acid | 13.8 | 1.322 |
| Glycine | 11.0 | 2.066 |
| Alanine | 7.3 | 1.155 |
| Valine | 6.4 | 0.771 |
| Methionine | 2.5 | 0.236 |
| Isoleucine | 2.5 | 0.269 |
| Leucine | 7.0 | 0.753 |
| Tyrosine | 5.8 | 0.451 |
| Phenylalanine | 12.8 | 1.050 |
| Lysine | 2.2 | 0.212 |
| Histidine | 1.0 | 0.091 |
| Trypophan | trace | — |
| Arginine | trace | — |
| Ammonium | 0.5 | — |

It is seen from Table 4 that the protein fragment of the HGI-glycoprotein is composed of 17 amino acids of which acidic and neutral amino acids dominante, while basic amino acids are minor constituents. It is also one of the characteristics that over 70% of the total amino acids are linear amino acids including aspartic acid, threonine, serine, glutamic acid, glycine, alanine, valine and leucine.

(10) Electrophoresis

Figure 2:
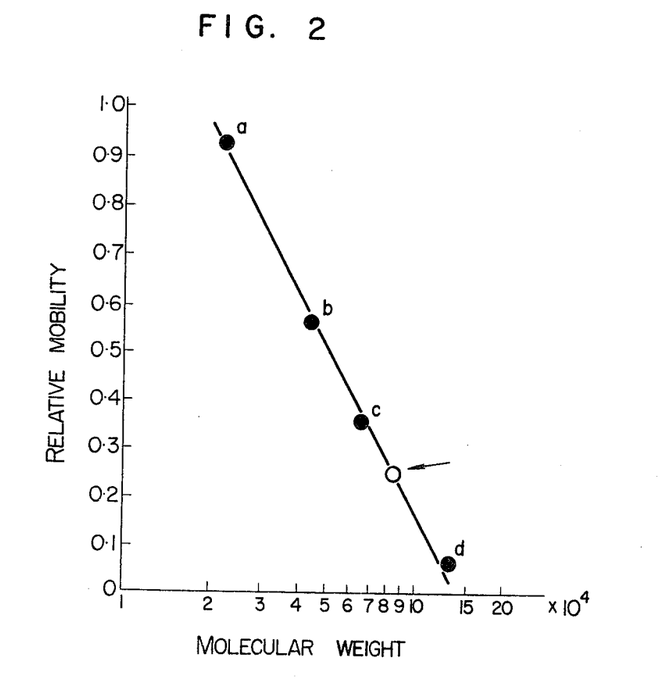
FIG. 2 shows the correlation between the relative mobility in electrophoresis and the molecular weight.

By following the Laemuli's method [Nature, Vol. 227, p. 680 (1970)] and using a sodium dodecyl sulfate-polyacrylamide gel, the HGI-glycoprotein which shows single band at a position of relative mobility of 0.25, trypsin inhibitor (molecular weight 21,500), ovalbumin (molecular weight 43,000), human serum albumin monomer (molecular weight 65,000) and human serum albumin dimer (molecular weight 130,000) were simultaneously electrophored. From the mobilities of the substances having known molecular weights and that of the HGI-glycoprotein, the molecular weight of the latter was found to be about 85,000 (FIG. 2). In FIG. 2, a, b, c and d represent trypsin inhibitor, ovalbumin, human serum albumin monomer, and human serum albumin dimer, respectively, and the arrow represents the HGI-glycoprotein.

(11) Ultraviolet absorption spectrum

Figure 3:
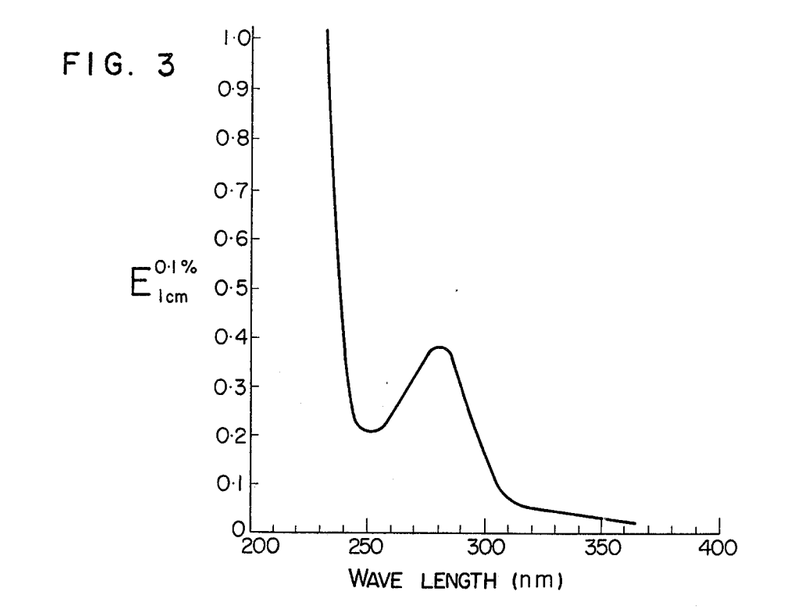
FIG. 3 shows ultraviolet absorption spectrum of the HGI-glycoprotein.

Ultraviolet absorption spectrum of the HGI-glycoprotein, as measured on a 0.1% aqueous solution in a 1 cm silica cell, is shown in FIG. 3. It shows the maximum absorption at 280 nm and terminal absorption in the wave length region shorter than 250 nm. The optical density $E_{1\ cm}^{1\%}$ at 280 nm is 3.8.

(12) Sugar composition of polysaccharide fragment

Neutral sugars were determined by the phenol-sulfuric acid reaction, sialic acids by the Warren's thiobarbital method [Journal of Biological Chemistry, Vol. 234, p. 1971 (1959)], and amino sugars by the Elson-Morgan method [Biochemical Journal, Vol. 27, p. 1824 (1933)]. The weight of neutral sugars were expressed in terms of glucose. The results were as follows: neutral sugars: 10.0–13.0%; sialic acids: 3.0–7.0%; amino sugars: less than 1.0%; total sugar: 13.0–20.0%.

(13) Composition ratio of protein and polysaccharide

The protein content of HGI-glycoprotein is 75–85%, as determined by the semi-micro kjeldahl method. The total sugar content is 13.0–20.0%, as described above.

(14) Elementary analysis

The results of elementary analysis of HGI-glycoprotein are as follows: C, 42.3–47.3%; H, 5.7–7.8%; N, 9.6–14.3%; O, 34.4–39.4%; S, less than 0.2%.

The HGI-glycoprotein of the above physical and chemical characteristics has a function of stimmulating the proliferation and differentiation of both human and mouse granulocytes as seen from Test 1 (described later) and shows no acute toxicity as evidenced by Test 4 (described later). Further, as is apparent from the results of Test 3 (described later), it can be utilized as leukopenia chemotherapeutics.

The HGI-glycoprotein prepared from human urine by the aforesaid procedure is aseptically lyophilized in vials and hermetically sealed. It is also possible, prior to the lyophilization, to add to the HGI-glycoprotein an aqueous solution containing human serum albumin as stabilizer and an amino acid or a saccharide as solubilizing aid; the resulting solution is sterilized by membrane filtration and then aseptically lyophilized. Before using, the vial is unsealed and the HGI-glycoprotein is dissolved by adding sterilized physiological saline solution, sterile water or a sterile isotonic solution. The resulting solution is administered to the patient with leukopenia by intravenous, intramuscular or subcutaneous injection.

From the results of Tests 1 and 2 (described later), the effective dose is 0.75 mg or more, preferably 0.75 to 2.24 mg, per day per kg of body weight. Semi-purified products, prepared on a large scale, having a specific biological activity of 35,000 units/mg or more such as those containing HGI-glycoprotein corresponding to sample No. 4 and No. 5 of Example 1 (described later) may also be used as pharmaceuticals.

The effect of HGI-glycoprotein on the proliferation and differentiation of granulocytes is described below in detail.

Test 1

Stimulating effects on proliferation and differentiation of mouse and human granulocytes in vitro.

Figure 4:
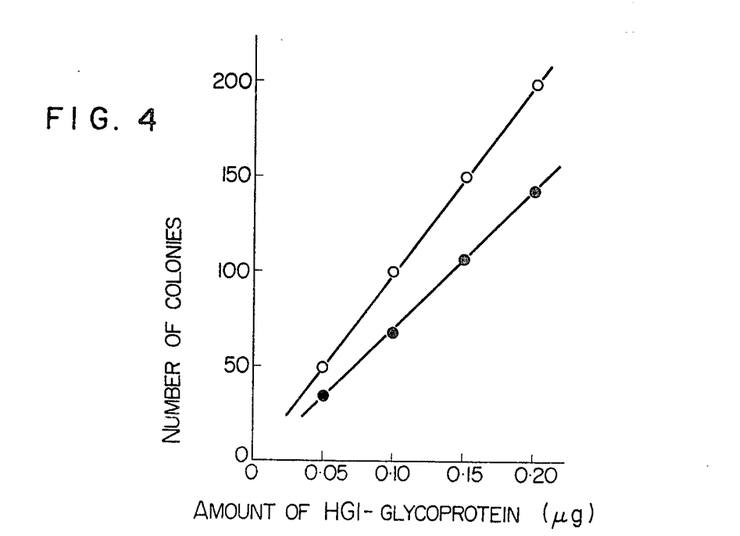
FIG. 4 shows the relationship between the addition amount of the HGI-glycoprotein and the number of colonies developed in vitro assay.

In each plastic Petri dish, 35 mm in diameter, was placed 1 ml of McCoy's 5A medium containing 0.05, 0.1, 0.15 or 0.2 μg of HGI-glycoprotein (sample No. 6 of Example 1), 20% of fetal calf serum, 0.3% of agar and $7.5 \times 10^4$ mouse bone marrow cells or $25 \times 10^4$ bone marrow cells of normals or patients with iron-deficiency anemia. The medium in the Petri dish was incubated in a humidified 5% $CO_2$ atmosphere at 37° C. for 7 to 9 days. The difference in the number of introduced cells between the mouse and man was due to a greater number of committed stem cells in the case of mouse. After incubation, discrete colonies containing more than 50 cells for mouse or more than 40 cells for human were counted with an inverted microscope. For morphologic analysis of colonies, some of them were picked up with microhematocrit tubes and stained with 0.6% orcein in 40% acetic acid. The results obtained were as shown in FIG. 4. FIG. 4 shows the interrelationship between the dose of HGI-glycoprotein and the number of colonies which were formed in vitro. In FIG. 4, -•-•- pertains to the mouse bone marrow cell and -••- to the human bone marrow cell.

As is apparent from FIG. 4, HGI-glycoprotein stimulates the proliferation and differentiation of bone marrow cells of mouse and man, thereby forming colonies and there are dose-response relationship between HGI-glycoprotein and formed colony numbers.

On the morphologic analysis of the cells formed colonies, it was observed that these cells were all mature granulocytes.

As described above, HGI-glycoprotein acts on both human and mouse bone marrow cells to form colonies of granulocytes, the number of colonies being proportional to the dose of HGI-glycoprotein, and there is a definite relationship in the formation of colonies of bone marrow cells between mouse and man. Therefore, in all of the following experiments, only mouse bone marrow cells were employed.

Test 2

Stimulating effects on proliferation and differentiation of granulocyte in vivo.

Sixty $C_{57}BL$ male mice (20 g of average body weight) were divided at random into 6 groups of each 10 members. One group, which served as control, was subcutaneously adminstered with 0.04 mg/mouse of human serum albumin dissolved in 0.2 ml of sterile normal saline solution, once a day, for 3 consecutive days. The remaining 5 experimental groups, i.e. 1st, 2nd, 3rd, 4th and 5th group, were subcutaneously administered respectively with 0.005, 0.01, 0.02, 0.03 and 0.04 mg/mouse of HGI-glycoprotein (sample No. 6 of Example 1 described later) each dissolved in 0.2 ml of sterile normal saline solution, once a day, for 3 consecutive days.

Blood samples were collected from the vena coccygea of each mouse before administration and 2, 4, 6, 8 and 10 days after administration. The leukocytes of each blood sample were stained with 1% gentiana violet solution and leukocyte numbers were counted with a Bürker-Türk counting chamber.

Further, each blood sample was smeared on a slide glass, stained with Wright-Giemsa solution, and the proportion of granulocytes in leukocytes was measured under a microscope.

The number of granulocytes was calculated by the following formula:

$$\begin{pmatrix}\text{number of leukocytes} \\ \text{in 1 mm}^3\end{pmatrix} \times \begin{pmatrix}\text{proportion of granulocytes} \\ \text{in leukocytes}\end{pmatrix} = $$

number of granulocytes in 1 mm$^3$.

The results obtained were as shown in Table 5.

TABLE 5

| | Group | | | | | |
|---|---|---|---|---|---|---|
| | Control | 1st | 2nd | 3rd | 4th | 5th |
| | | | Dose (mg) | | | |
| Days | 0 | 0.005 | 0.01 | 0.02 | 0.03 | 0.04 |
| 0 | 450 | 452 | 455 | 450 | 448 | 445 |
| 2 | 380 | 420 | 550 | 600 | 775 | 800 |
| 4 | 372 | 390 | 800 | 1100 | 1400 | 1420 |
| 6 | 380 | 395 | 1100 | 1800 | 2200 | 2100 |
| 8 | 410 | 400 | 620 | 750 | 980 | 971 |
| 10 | 430 | 410 | 470 | 460 | 465 | 480 |

Note:-
Each numerical value represents mean number of granulocytes per mm$^3$ for 10 mice.

As shown in Table 5, it is indicated that the peripheral granulocyte counts of the experimental groups administrated with 0.01–0.04 mg/mouse of the HGI-glycoprotein began to increase after 2 days of administration and reached to 3–6 times of the count of control groups after 6 days.

The granulocyte counts decreased and returned to the normal level at 10 days. When the daily dose was increased to excess 0.04 mg, there were no significant increase of granulocytes corresponding to increasing dose of the HGI-glycoprotein.

These results suggested that the granulocytosis can be sufficiently produced by daily injection of 0.01 mg or more, preferably 0.01–0.03 mg, of HGI-glycoprotein to a mouse (mean body weight is approximately 20 g). However, since the stimulating effect of HGI-glycoprotein on mouse bone marrow cells in vitro is an average of about 1.5 times higher than the effect on human bone marrow cells (Test 1), the effective dose for man is presumed to be 1.5 times as high as that for mouse determined in vivo in Test 2. Accordingly, the effective daily dose per kg of body weight for man is estimated as 0.75 mg or more, preferably 0.75 to 2.24 mg.

Test 3

Protective effect of HGI-glycoprotein on leukopenia caused by carcinostatic substances.

Thirty C$_{57}$BL male mice, 4–5 weeks old, were divided at random into 3 groups of 10 members. The control group was administered by intraperitoneal injection with 30 mg/kg body weight (equivalent to (1/10) LD$_{50}$) of cytosine-D-arabinoside dissolved in 0.2 ml of sterile normal saline solution, once a day, for 14 consecutive days. In addition, 0.2 ml/mouse of sterile normal saline solution was subcutaneously administered once a day for 14 consecutive days. Another group (HGI-leucoprotein administered group) was administered with cytosine-D-arabinoside in the same manner as in the control group. In addition, 0.03 mg/mouse of HGI-glycoprotein (sample No. 6 of Example 1 described later) was subcutaneously administered once a day for 14 consecutive days. The remaining group (Cepharantine administered group) was administered with cytosine-D-arabinoside in the same manner as in the control group and further administered subcutaneously with 0.3 mg/mouse of Cepharantine (Kaken Pharmaceuticals Co.; conventionally employed for leukopenia) dissolved in 0.2 ml of sterile normal saline solution, once a day for 14 consecutive days.

Blood samples were collected from the vena coccygea of each mouse before administration and 2, 4, 6, 8, 10, 12 and 14 days after administration. The number of leukocytes was measured as in Test 2 and the percentage decrease (decrement) in number of leukocytes after administration was obtained by assuming the count before administration as 100. The results were shown in Table 6.

TABLE 6

| | Group | | | | | |
|---|---|---|---|---|---|---|
| | Control | | HGI-glycoprotein administered | | Cepharantine administered | |
| Days after administration | Leucocyte count ($\times 10^2$/mm$^3$) | Decrement (%) | Leucocyte count ($\times 10^2$/mm$^3$) | Decrement (%) | Leucocyte count ($\times 10^2$/mm$^3$) | Decrement (%) |
| Before administration | 150 | 100 | 150 | 100 | 150 | 100 |
| 2 | 130 | 86.6 | 120 | 80.0 | 125 | 83.3 |
| 4 | 125 | 83.3 | 125 | 83.3 | 120 | 80.0 |
| 6 | 120 | 80.0 | 130 | 86.6 | 120 | 80.0 |
| 8 | 110 | 73.3 | 120 | 80.0 | 110 | 73.3 |
| 10 | 95 | 63.3 | 120 | 80.0 | 100 | 66.6 |
| 12 | 80 | 53.3 | 115 | 76.6 | 105 | 70.0 |
| 14 | 70 | 46.6 | 110 | 73.3 | 95 | 63.3 |

Note:-
Each numerical value is an average for 10 mice.

As compared with the control group, the HGI-glycoprotein administered group showed a marked preventive effect on the reduction in leucocyte count after ten days from the beginning of the HGI-glycoprotein administration, the effect being comparable or superior to that of Cepharantine. On the 14th day from the beginning of administration, the leukocyte count of the control group was reduced to 46.6%, whereas that of the HGI-glycoprotein administered group was 73.3%, the decrement beging less than that of the Cepharantine administered group. Therefore, it is presumable that the HGI-glycoprotein will be effective for the therapy of human leukopenia.

It was also confirmed that the HGI-glycoprotein is also effective when other carcinostatic substances such as, for example, 5-fluorouracil and daunomycin were administered which have been known to cause reduction in leukocyte count similarly to cytosine-D-arabinoside. No preventive effect on the reduction in leukocyte count was observed when human serum albumin was examined in the same manner as described above.

Test 4

Acute toxicity of the HGI-glycoprotein.

The acute toxicity of HGI-glycoprotein prepared in Example 1 (samples No. 4 and No. 6) was tested on $C_{57}BL$ male mice by the method of Lichied and Wilcoxon [Journal of Pharmacology and Experimental Therapeutics, Vol. 90, p. 99 (1949)]. No fatal case was found when 4,000 mg/kg body weight was administered intraperitoneally or 2,000 mg/kg body weight was administered intravenously. Consequently, estimation of $LD_{50}$ was practically impossible, $LD_{50}$ of subcutaneous injection was above 4,000 mg/kg body weight and $LD_{50}$ of intravenous injection was above 2,000 mg/kg of body weight.

EXAMPLE 1

Four hundred liters of fresh urine collected from normal humans was adjusted to pH 8 with 10% sodium hydroxide and centrifuged by means of a continuous centrifugation at 15,000 r.p.m. at 0° C. to remove insolubles. The supernatant was adjusted to pH 7 with 10% hydrochloric acid and passed through a silica gel column (10×80 cm). The substances adsorbed or the silica gel were eluted with 40 liters of 5% ammonium solution. The eluted solution was adjusted to pH 7.5 with 1 N sulfuric acid, and added with ammonium sulfate to 70% saturation, and left standing at 0° C. for overnight. The precipitate was collected by filtration, dissolved in 2 liters of 5% ammonium solution, placed in cellophane tubes (Visking Co.) and dialized against 0.05 M phosphate buffer solution (pH 6.5). The dialized solution was mess up to 10 liters with the same buffer solution and passed through the CM Sephadex C-50 ® ion exchange column (40×40 cm) which had been equilibrated with 0.05 M phosphate buffer solution (pH 6.5), to adsorb the contaminants on the ion exchange resin. Ten liters of the effluent solution was concentrated by means of DIAFLO hollow fiber ultrafiltration apparatus (Amicon DC-30, U.S. molar weight cut off approximately 10,000). The concentrated solution was dialized against 0.1 M tris-HCl buffer (pH 7.0) at 5° C. for overnight. The dialized solution was made up to one liter with the same buffer solution (the resulting solution is referred to as sample No. 1).

The above solution was passed through the DEAE cellulose column (4.0×40 cm) which had been equilibrated with 0.1 M tris-HCl buffer (pH 7.0) and washed the column with sufficient volume of 0.1 M tris-HCl buffer (pH 7.0). The loaded column was carried out the step wise elution with 0.1 M tris-HCl buffer solution (pH 7.0) containing 0.3 M sodium chloride. The fractions capable of effecting proliferation and differention of granulocyte, as tested in the same manner as in Test 1, were collected and dialized against 0.1 M tris-HCl buffer (pH 7.0) (this solution is referred to as sample No. 2).

The dialized solution was again passed through DEAE cellulose column (4.0×40 cm) which had been equilibrated with 0.1 M tris-HCl buffer (pH 7.0) and the loaded column was carried out the linear concentration gradient with elution sodium chloride (0 to 0.3 M). The active fractions were collected and added with ammonium sulfate to 70% saturation. The precipitates were collected by centrifugation and dissolved in a small volume of 0.1 M tris-HCl buffer (pH 7.0) and dialized against the same buffer solution (this dialized solution is referred to as sample No. 3).

Twenty milliliters of the dialized solution was applied to Sephadex G-150 column (4.0×60 cm) which had been equilibrated with 0.1 M tris-HCl buffer (pH 7.0) and the effluent fractions obtained at Ve/Vo ratios of 1.11–1.45 were collected. The combined fraction was thoroughly dialized against distilled water at 5° C. and the dialized solution was lyophilized to obtain about 500 mg of a powder (this semi-purified HGI-glycoprotein is referred to as sample No. 4).

Two hundred milligrams of the semi-purified HGI-glycoprotein was dissolved in 0.02 M phosphate buffer (pH 7.0) containing 1.0 M sodium chloride and passed through 100 ml of concanavalin A-Sepharose 4B affinity column which had been equilibrated with the same buffer. After thorough washing of the column with the same buffer, the HGI-glycoprotein was eluted with 0.02 M phosphate buffer (pH 7.0) containing 50 mM α-methyl-D-glucoside and 1.0 M sodium chloride. The fractions which is capable of effecting proliferation and differentiation of granulocyte in vitro were collected and dialized against distilled water. The dialized solution was lyophilozed (this is referred to as sample No. 5).

About 50 mg of the above lyophilized powder was dissolved in 1 ml of 0.125 M tris-glycine buffer (pH 6.8) containing 10% glycerine. The resulting solution was electrophored at 10 mA under cooling by means of a preparative electrophoresis apparatus (Type Fuji Kabara II of Fuji Riken Co., Japan) employing 8% acrylamide gel (pH 8.9; 20 mm×25 mm). The fraction with a relative mobility of 0.46 was recovered with 0.025 M tris-glycine buffer (pH 8.3) and was dialized against distilled water. The dialized solution was lyophilized to obtain about 10 mg of the HGI-glycoprotein (which is referred to as sample No. 6).

The samples No. 1 to No. 6 obtained in various stages of preparation were tested for the proliferation and differentiation effect on both human and mouse bone marrow cells in a manner similar to that in Test 1. The HGI-glycoprotein or a fraction containing same was added to the medium in an amount necessary to form 200 colonies per dish. The specific activity was calculated by the following formula, wherein one unit corresponds to one colony formed:

Specific activity (units/mg) = $\frac{\text{Number of colonies formed (units)}}{\text{protein content (mg) of assayed sample}}$ The results were as shown in Table 7.

TABLE 7

| | Mouse bone marrow cell assy | | Human bone marrow cell assy | |
|---|---|---|---|---|
| Sample | Specific activity (units/mg) | Fold purification | Specific activity (units/mg) | Fold purification |
| No. 1 | 260 | 1 | 160 | 1 |
| No. 2 | 4,500 | 17.3 | 2,200 | 13.8 |
| No. 3 | 11,000 | 42.3 | 5,500 | 34.4 |
| No. 4 | 57,000 | 219.2 | 35,000 | 218.8 |
| No. 5 | 210,000 | 807.7 | 180,000 | 1125.0 |
| No. 6 | 1,000,000 | 3846.1 | 670,000 | 4187.5 |

EXAMPLE 2

To 100 mg of HGI-glycoprotein powder (sample No. 6) obtained in the same way as in Example 1, was added 100 ml of an aqueous solution containing 5% human serum albumin (Sigma Co., United States) and 1% glycine (Wako Pure Chemicals Co., Japan). The resulting solution was sterlized by Millipore filtration system (Millipore Co., United States) provided with membrane filters of 0.45µ pore size. The sterilized solution was aseptically filled, in 1 ml portions, in vials which had been sterlized by heating at 180° C. for 2 hours. After lyophilization, the vials were hermetically sealed. In this way, ther were obtained 95 vials of a therapeutic agent for leukopenia, each vial containing 1 mg of HGI-glycoprotein.

EXAMPLE 3

In a same manner to that in Example 1, one liter of a concentrated solution containing HGI-glycoprotein, which was analogous to sample No. 1, was prepared from 1,000 liters of fresh urine collected from normal humans. To this concentrated solution was diluted with 10 liters of 0.1 M tris-HCl buffer (pH 7.0). After thorough stirring, the diluted solution was reconcentrated to about one-tenth of the original volume by use of DIAFLO® hollow fiber ultrafiltration apparatus. The concentrated solution was added 5 liters of 0.1 M tris-HCl buffer (pH 7.0) and 5 liters of DEAE cellulose suspension containing 300 g on dry basis of DEAE cellulose, which had been equilibrated with 0.1 M tris-HCl buffer (pH 7.0). The mixture was stirred for 30 minutes, stand for 10 minutes and filtrated under vacuum on a Buchner funnel to collect the DEAE cellulose. The collected DEAE cellulose was washed with 10 liters of 0.1 M tris-HCl buffer (pH 7.0) and recollected by filtration as same as above. The DEAE cellulose was further washed with 10 liters of 0.1 M tris-HCl buffer (pH 7.0) containing 0.05 M sodium chloride and recollected by same manner as above. The DEAE cellulose thus treated, was added with 10 liters of 0.1 M tris-HCl buffer (pH 7.0) containing 0.3 M sodium chloride and stirred to free the HGI-glycoprotein from the DEAE cellulose. The mixture was filtrated by same manner as above and filtrated solution was collected. The filtrated solution was desalted by DIAFLO hollow fiber ultrafiltration. The desalted solution was lyophilized to collect about 15 g of a powder. The powder was dissolved in 150 ml if distilled water and applied to Sephadex G-150 column (6.0×80 cm) which had been quilibrated with 0.1 M tris-HCl buffer (pH 7.0). The fractions corresponding to Ve/Vo ratios of 1.11–1.60 were collected. The combined fraction was thoroughly dialized against distilled water. The dialized solution was concentrated by DIAFLO hollow fiber concentration apparatus (Type DC-2) to about 100 ml of a concentrate containing about 3 g of crude HGI-glycoprotein. The concentrated solution was added with 1 g of glycine (Wako Pure Chemicals Co.) and 5 g of serum albumin (Sigma Co.). The resulting solution was sterilized by filtration in the same manner as in Example 1 and aseptically filled, in 2.5 ml portions, in vials. After aseptic lyophilization, the vials were hermetically sealed. Thus, there were obtained 40 vials of a therapeutic agent for leukopenia, each vial containing about 3.8 mg of the HGI-glycoprotein.

What is claimed is:

1. A glycoprotein in pure form from the urine of normal humans, which stimulates human bone marrow cells to form colonies of granulocytes, which has a molecular weight of 75,000 to 90,000 dalton as determined by gel filtration, which has an isoelectric point of pH $4.7\pm0.2$ and which contains 78–85% by weight of protein and 13.0–20.0% by weight of polysaccharide.

2. A glycoprotein according to claim 1, which is soluble in water, slightly soluble in chloroform and insoluble in ethyl alcohol and acetone.

3. A glycoprotein according to claim 1, which has a specific (optical) rotation $[\alpha]_D^{20}$ of $0\pm40$ in a 0.25% aqueous solution.

4. A glycoprotein according to claim 1, which shows pH 5.0 to 6.0 in 1% aqueous solution.

5. A glycoprotein according to claim 1, which loses completely the stimulating function on the proliferation and differentiation of human granulocytes, when heated in 1% aqueous solution at $60°\pm0.5°$ C. for 30 minutes.

6. A glycoprotein according to claim 1, which has a relative mobility of 0.25 in the electrophoresis utilizing sodium dodecyl sulfate-polyacrylamide gel.

7. A glycoprotein according to claim 1, which shows in infrared absorption spectrum characteristic absorption at wave numbers ($cm^{-1}$) of 3600–3200 (strong), 1700–1600 (strong), 1550 (medium), 1430–1380 (medium), and 1150–1000 (broad).

8. A glycoprotein according to claim 1, which produces a color characteristic of saccharides in the $\alpha$-naphthol-sulfuric acid reaction, indole-sulfuric acid reaction, anthrone-sulfuric acid reaction and phenolsulfuric acid reaction and a color characteristic of amino and polypeptide linkages in the Lowry-Folin's reaction and in the ninhydrin reaction after hydrolysis with hydrochloric acid.

9. A glycoprotein according to claim 1, wherein the constituent amino acids of the protein moiety are proline, aspartic acid, threonine, serine, glutamic acid, glycine, alanine, valine, methionine, isoleucine, leucine, tyrosine, phenylaline, lysine, histidine, tryptophan and arginine.

10. A glycoprotein according to claim 1, which is white in color and amorphous in shape.

11. A glycoprotein according to claim 1, wherein the sugar composition of the polysaccharide moiety is 10.0–13.0% by weight in terms of glucose of neutral sugars, 3.0–7.0% by weight of sialic acids and less than 1% by weight of other amino sugars.

12. A glycoprotein according to claim 1, which gives on elementary analysis the following results: 42.3–47.3% of carbon, 5.7–7.8% of hydrogen, 9.6–14.3% of nitrogen, 34.4–39.4% of oxygen and 0.2% or less of sulfur.

13. A therapeutic agent for leukopenia containing as active material a glycoprotein according to claim 1.

14. A therapeutic agent for leukopenia containing as active material a glycoprotein according to claim 1 having a specific biological activity of 35,000 units/mg or more.

15. A process for producing a glycoprotein which stimulates human bone marrow cells to form colonies of granulocytes, which comprises concentrating urine of normal human with respect to proteins contained therein, contacting the urinary proteins with a cation exchanger to remove impurities by adsorption on said exchanger, contacting the effluent with an anion exchanger to adsorb the active material, eluting the active material with a saline solution according to linear concentration gradient elution, subjecting the eluate to gel filtration chromatography on a highly crosslinked polymer gel to develop the active material, and collecting fractions of a relative effluent of 1.11 to 1.60.

16. A process for producing a glycoprotein which stimulates human bone marrow cells to form colonies of granulocytes, which comprises concentrating urine of normal humans with respect to proteins contained therein, contacting the urinary proteins with a cation exchanger to remove impurities by adsorption on said exchanger, contacting the effluent with an anion exchanger to adsorb the active material, eluting the active material with a saline solution according to linear concentration gradient elution, subjecting the eluate to gel filtration chromatography on a highly crosslinked polymer gel to develop the active material, collecting fractions of a relative effluent of 1.11 to 1.60, subjecting the collected fractions to affinity chromatography with a sugar affinitive absorbent to adsorb the active material, eluting the adsorbed active material with a 20–100 mM saccharide solution.

17. A process for producing a glycoprotein which stimulates human bone marrow cells to form colonies of granulocytes, which comprises concentrating urine of normal humans with respect to proteins contained therein, contacting the urinary proteins with a cation exchanger to remove impurities by adsorption on said exchanger, contacting the effluent with an anion exchanger to adsorb the active material, eluting the active material with a saline solution according to linear concentration gradient elution, subjecting the eluate to gel filtration chromatography on a highly crosslinked polymer gel to develop the active material, collecting fractions of a relative effluent of 1.11 to 1.60, subjecting the collected fractions to affinity chromatography with a sugar affinitive absorbent to adsorb the active material, eluting the adsorbed active material with a 20–100 mM saccharide solution, subjecting the eluate to preparative zone electrophoresis, eluating the active material with saline solution to recover the active material in pure form.

18. A process for producing the glycoprotein of claim 16, wherein the relative effluent volume is 1.11–1.45.

19. A glycoprotein in pure form from normal human urine which stimulates human bone marrow cells to form colonies of granulocytes and which has the following physical and chemical properties:
(a) solubility: soluble in water, slightly soluble in chloroform, and insoluble in ethyl alcohol and acetone;
(b) specific optical rotation: $[\alpha]_D^{20} = 0 \pm 40$ (0.25% aqueous solution);
(c) pH: 5.0–6.0 (1% by weight aqueous solution);
(d) isoelectric point: pH 4.7±0.2;
(e) thermostability: on being heated at 60°±0.5° C. for 30 minutes in 1% aqueous solution, the stimulating function on the proliferation and differentiation of the human granulocyte is completely lost;
(f) electrophoresis: the relative mobility is 0.25 in the electrophoresis using sodium dodecyl sulfatepolyacrylamide gel;
(g) infrared absorption: characteristic absorption at the following wave numbers (cm$^{-1}$): 3600–3200 (strong absorption), 1700–1600 (strong absorption), 1550 (medium absorption), 1430–1380 (medium absorption), and 1150–1000 (broad band);
(h) color reaction: colors characteristic of saccharides are produced by the α-naphthol-sulfuric acid reaction, indole-sulfuric acid reaction, anthronesulfuric acid reaction and phenol-sulfuric acid reaction; colors characteristic of polypeptide linkage and amino acids are produced by the Lowry-Folin's reaction and by the ninhydrin reaction after hydrolysis with hydrochloric acid;
(i) constituent amino acids of the protein moiety: proline, aspartic acid, threonine, serine, glutamic acid, glycine, alanine, valine, methionine, isoleucine, leucine, tyrosine, phenylalanine, lysine, histidine, tryptophan and arginine;
(j) color and shape: substantially white and amorphous;
(k) sugar composition of the polysaccharide moiety: 10.0–13.0% by weight in terms of glucose of neutral sugars, 3.0–7.0% by weight of sialic acids and less than 1% by weight of other amino sugars.
(l) weight ratio of protein to polysaccharide: 75–85: 13.0–20.0;
(m) elementary analysis: 42.3–47.3% of carbon, 5.7–7.8% of hydrogen, 9.6–14.3% of nitrogen, 34.4–39.4% of oxygen and 0.2% or less of sulfur; and
(n) molecular weight: 75,000 to 90,000 dalton as determined by gel filtration.

20. A method of treating leukopenia comprising administering to an individual having leukopenia sufficient of the compound of claim 1 to have a preventive effect on the reduction of leucocyte count.

21. A process for stimulating human bone marrow cells to form colonies of granulocytes comprising supplying to the bone marrow an amount of the glycoprotein of claim 1 effective to increase the colonies of granulocytes.

22. A glycoprotein in a purity capable of being administered to an individual having leukopenia, which is produced by the process of claim 15.

23. A glycoprotein in a purity capable of being administered to an individual having leukopenia, which is produced by the process of claim 16.

24. A glycoprotein in a purity capable of being administered to an individual having leukopenia, which is produced by the process of claim 15 or 16, and which has the following physical and chemical properties:
(a) solubility: soluble in water, slightly soluble in chloroform, and insoluble in ethyl alcohol and acetone;
(b) specific optical rotation $[\alpha]_D^{20} = 0 \pm 40$ (0.25% aqueous solution);
(c) pH: 5.0–6.0 (1% by weight aqueous solution);
(d) isoelectric point: pH 4.7±0.2;
(e) thermostability: on being heated at 60°±0.5° C. for 30 minutes in 1% aqueous solution, the stimulating function on the proliferation and differentiation of the human granulocyte is completely lost;
(f) electrophoresis: the relative mobility is 0.25 in the electrophoresis using sodium dodecyl sulfatepolyacrylamide gel;
(g) infrared absorption: characteristic absorption at the following wave numbers (cm$^{-1}$): 3600–3200 (strong absorption), 1700–1600 (strong absorption), 1550 (medium absorption), 1430–1380 (medium absorption), and 1150–1000 (broad band);
(h) color reaction: colors characteristic of saccharides are produced by the α-naphthol-sulfuric acid reaction, indole-sulfuric acid reaction, anthrone-sulfuric acid reaction and phenol-sulfuric acid reaction; colors characteristic of polypeptide linkage and amino acids are produced by the Lowry-Folin's reaction and by the ninhydrin reaction after hydrolysis with hydrochloric acid;

(i) constituent amino acids of the protein moiety: proline, aspartic acid, threonine, serine, glutamic acid, glycine, alanine, valine, methionine, isoleucine, leucine, tyrosine, phenylalanine, lysine, histidine, triptophan and arginine;

(j) color and shape: substantially white and amorphous;

(k) sugar composition of the polysaccharide moiety: 10.0-13.0% by weight in terms of glucose of neutral sugars, 3.0-7.0% by weight of sialic acids and less than 1% by weight of other amino sugars;

(l) weight ratio of protein to polysaccharide: 75-85: 13.0-20.0;

(m) elementary analysis: 42.3-47.3% of carbon, 5.7-7.8% of hydrogen, 9.6-14.3% of nitrogen, 34.4-39.4% of oxygen and 0.2% or less of sulfur; and (n) molecular weight: 75,000 to 90,000 dalton as determined by gel filtration.

* * * * *